United States Patent
Messroghli

(10) Patent No.: US 9,008,753 B2
(45) Date of Patent: Apr. 14, 2015

(54) LOOK-LOCKER IR-SSFP FOR CARDIAC MR IMAGING WITH SIMULTANEOUS GENERATION OF CARDIAC T1 MAPS, CINE IMAGES AND IR-PREPARED IMAGES

(75) Inventor: Daniel Messroghli, Berlin (DE)

(73) Assignee: Deutsches Herzzentrum Berlin, Berlin (DE)

( * ) Notice: Subject to any disclaimer, the term of this patent is extended or adjusted under 35 U.S.C. 154(b) by 346 days.

(21) Appl. No.: 13/509,273

(22) PCT Filed: Nov. 10, 2010

(86) PCT No.: PCT/EP2010/067191
§ 371 (c)(1),
(2), (4) Date: May 27, 2012

(87) PCT Pub. No.: WO2011/058047
PCT Pub. Date: May 19, 2011

(65) Prior Publication Data
US 2012/0232378 A1    Sep. 13, 2012

Related U.S. Application Data

(60) Provisional application No. 61/259,680, filed on Nov. 10, 2009.

(51) Int. Cl.
*A61B 5/055*     (2006.01)
*G01R 33/50*     (2006.01)
(Continued)

(52) U.S. Cl.
CPC .............. *G01R 33/50* (2013.01); *A61B 5/055* (2013.01); *G01R 33/4818* (2013.01);
(Continued)

(58) Field of Classification Search
CPC .............. A61B 5/055; G01R 33/4818; G01R 33/4824; G01R 33/50; G01R 33/5602; G01R 33/56308; G01R 33/56325; G01R 33/5614; G01R 33/5673; G01R 33/5619
See application file for complete search history.

(56) References Cited

U.S. PATENT DOCUMENTS

| | | | | |
|---|---|---|---|---|
| 5,908,386 A | * | 6/1999 | Ugurbil et al. | 600/410 |
| 6,487,435 B2 | * | 11/2002 | Mistretta et al. | 600/420 |
| 6,954,067 B2 | * | 10/2005 | Mistretta | 324/307 |
| 8,060,180 B2 | * | 11/2011 | Pai | 600/410 |

(Continued)

OTHER PUBLICATIONS

Messroghli et al. "Assessment of Diffuse Myocardial Fibrosis in Rats Using Small-Animal Look-Locker Inversion Recovery T1 Mapping." Circ Cardiovasc Imaging. Sep. 14, 2011;4:636-640.*

*Primary Examiner* — Long V Le
*Assistant Examiner* — Angela M Hoffa
(74) *Attorney, Agent, or Firm* — VLP Law Group LLP; Kent H. Cheng

(57) ABSTRACT

The present invention is directed to a method for use in conducting cardiac MR imaging which allows for reconstruction of T1 maps, cine images and IR-prepared images from one raw data set, wherein the method comprises the following steps: a) acquisition of raw data by use of an ECG-triggered, segmented, inversion recovery (IR) -prepared Look-Locker type pulse sequence for data acquisition, wherein the pulse sequence encompasses more than one shot, wherein each shot comprises: i) an ECG-triggered inversion pulse; ii) SSFP cine data acquisition of radial segmented profiles over more than one RR-interval for a predefined acquisition duration AD; and iii) a relaxation duration RD, during which no data is acquired; b) retrospective gating of raw data by sorting acquired raw data for each RR-interval into a pre-determined number of heart phases by definition of specific time windows within the RR-intervals and sampling of raw data acquired during the time windows respectively; c) image reconstruction, wherein the retrospectively gated raw data is used for reconstruction of T1 maps, cine images and/or IR-prepared images.

21 Claims, 10 Drawing Sheets

Figure 1:
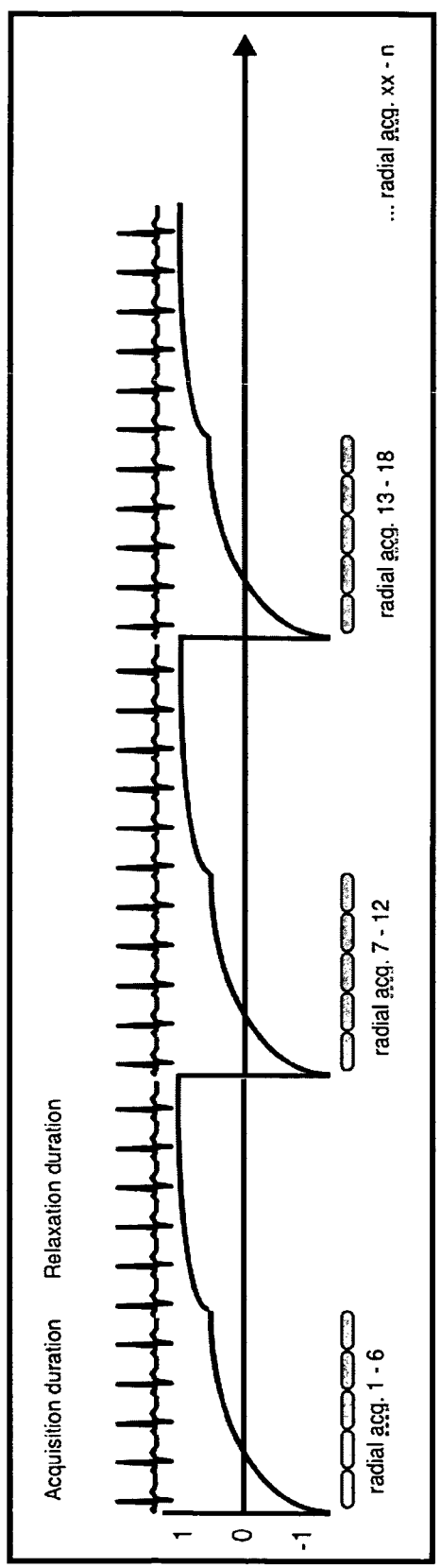

(51) Int. Cl.
*G01R 33/56* (2006.01)
*G01R 33/561* (2006.01)
*G01R 33/563* (2006.01)
*G01R 33/48* (2006.01)
*G01R 33/567* (2006.01)

(52) U.S. Cl.
CPC ....... *G01R 33/4824* (2013.01); *G01R 33/5602* (2013.01); *G01R 33/5614* (2013.01); *G01R 33/56308* (2013.01); *G01R 33/56325* (2013.01); *G01R 33/5619* (2013.01); *G01R 33/5673* (2013.01)

(56) References Cited

U.S. PATENT DOCUMENTS

| | | | |
|---|---|---|---|
| 8,073,522 B2 * | 12/2011 | Stemmer | 600/410 |
| 8,112,145 B2 * | 2/2012 | Grist et al. | 600/413 |
| 8,581,583 B2 * | 11/2013 | Greiser | 324/309 |
| 2003/0060698 A1 * | 3/2003 | Mistretta | 600/410 |
| 2004/0155653 A1 | 8/2004 | Larson et al. | |
| 2005/0245812 A1 | 11/2005 | Kim et al. | |
| 2005/0272997 A1 | 12/2005 | Grist et al. | |
| 2008/0150532 A1 * | 6/2008 | Slavin et al. | 324/318 |
| 2009/0275822 A1 | 11/2009 | Detsky et al. | |

\* cited by examiner

LOOK-LOCKER IR-SSFP FOR CARDIAC MR IMAGING WITH SIMULTANEOUS GENERATION OF CARDIAC T1 MAPS, CINE IMAGES AND IR-PREPARED IMAGES

RELATED APPLICATIONS

This is a U.S. national stage of application No. PCT/EP10/067191, filed on Nov. 10, 2010. Priority is claimed on the following application: U.S. Application Ser. No. 61/259,680 filed on Nov. 10, 2009, the contents of which is herein incorporated here by reference.

BACKGROUND OF THE INVENTION

T1 mapping provides quantitative information on tissue alterations and gadolinium kinetics. In the heart, the ability to identify myocardial edema and the potential to identify diffuse interstitial fibrosis are of particular interest.

Mapping of T1 relaxation times typically requires the acquisition of multiple images with different inversion times in order to allow for an accurate fitting of the underlying T1 curve. Dedicated cardiac T1 mapping schemes typically acquire a sufficient number of images within one breath-hold. Dedicated ECG (electrocardiogram)-triggered Look-Locker Inversion Recovery (IR) techniques have already been described for cardiac magnetic resonance (MR) imaging, see e.g. Messroghli et al., "Modified Look-Locker Inversion recovery (MOLLI) for High-Resolution T1 Mapping of the Heart", *Magn. Reson. Med.* (2004), 52: 141-146; and Messroghli et al., "Human Myocardium: Single-Breath-hold MR T1 Mapping with High Spatial Resolution—Reproducibility Study", *Radiology* (2006), 238: 1004-1012. However, such techniques use non-segmented acquisitions with durations of approximately 150 to 200 ms for each raw image. While it could be shown that this acquisition duration is adequate to acquire images at end-diastole for heart rates up to 100 beats per minute (bpm) with high reproducibility, this approach is not suitable for use in small animals where heart rates in the range of 200 to 600 bpm are to be expected. Consequently, alternative approaches are warranted for these situations, which usually lead to a significant rise in over-all acquisition time. This might not be desirable for imaging protocols where other types of MR images are to be collected within the same session, causing long scan times that might potentially exceed the limits where the animals can be studied safely under stable conditions.

SUMMARY OF THE INVENTION

It is an object of the present invention to provide a method that solves the problems of high heart rate and prolonged acquisition times and allows for the generation of T1 maps, cine, and inversion-recovery (IR)-prepared images from one single data set.

This object is achieved by the provision of a method for use in conducting cardiac MR imaging which allows for reconstruction of T1 maps, cine images and IR-prepared images from one single raw data set, wherein the method comprises the following steps:
a) acquisition of raw data by use of an ECG (electrocardiogram)-triggered, segmented, inversion recovery (IR)-prepared Look-Locker type pulse sequence for data acquisition, wherein the pulse sequence encompasses more than one shot, wherein each shot comprises:
  i) an ECG-triggered inversion pulse;
  ii) SSFP (steady-state free precession) cine data acquisition of radial segmented profiles over more than one RR-interval for a predefined acquisition duration AD; and
  iii) a relaxation duration RD, during which no data is acquired;
b) retrospective gating of raw data by sorting acquired raw data for each RR-interval into a pre-determined number of heart phases by definition of specific time windows within the RR-intervals and sampling of raw data acquired during the time windows respectively;
c) image reconstruction, wherein the retrospectively gated raw data is used for reconstruction of T1 maps, cine images and/or IR-prepared images.

After an ECG-triggered non-selective (adiabatic) inversion pulse, radial steady-state free precession (SSFP) cine data acquisition is performed over several cardiac cycles (RR-intervals) for a pre-determined period of time, the acquisition time AD. One shot comprises an acquisition duration AD during which SSFP cine data acquisition is performed continuously for one inversion. SSFP cine data acquisition comprises continuous data acquisition over the acquisition duration AD. Said continuous data acquisition is conducted with short repetition times (TR) and echo times (TE), preferably TR and TE are set to be as short as possible (the shortest TR and TE achievable by the device used for MR imaging), e.g. 5.2 ms and 2.2 ms, respectively. Upon completion of a subsequent waiting period, the relaxation duration RD, the whole process is continued with the next shot.

In the method of the invention, each profile acquired during the acquisition duration AD does comprise only part of the data necessary to give a fully sampled data set, i.e. radial segmented profiles are acquired, wherein the segment to be acquired by a profile is switched during the pulse sequence that at least each segment necessary to give a fully sampled data set is acquired once per pre-determined heart phase. There are several algorithms known that can be used for radial segmented profile acquisition, see e.g. Shankaranaryanan et al., "Segmented k-space and real-time cardiac cine MR imaging with radial trajectories", *Radiology* (2001), 827-836, and the skilled person has no difficulties in applying these to the method of the invention. In principle the whole area to be imaged is split in segments such that all segments together allow the reconstruction of the whole image area. The image space to be represented is split in n k-space trajectories, wherein each k-space trajectory represents a radial segment of the complete image space. Each single radial segmented profile acquired during the acquisition duration AD represents one or a minor number of k-space trajectories of the complete image room. During image reconstruction, the k-space data for the corresponding radial segmented profiles are transformed into the image space to give a full image data set of the area of interest. Key of radial segmented profile acquisition is that segmentation is performed such that in a given period of time, data for all relevant segments is collected in a reproducible manner so that for each profile it is known which segment is acquired and at which time point after the inversion pulse said profile has been acquired. Segmented data acquisition allows for reduction of the read-out length to a time interval necessary to acquire data for the specific segmented profile. Thus, the data acquisition window for each acquisition pulse can be reduced such that it fits to the heart rate of the organism to be imaged and can be set to be shorter than 200 ms.

In the method of the invention, the SSFP cine data acquisition of radial segmented profiles can be performed such that all radial segmented profiles acquired during one shot cover the same radial segment and the radial segment to be acquired is switched between subsequent shots.

Alternatively, in the method of the invention the SSFP cine data acquisition of radial segmented profiles can be performed such that a temporal undersampling factor R is set; during raw data acquisition in each RR-interval, radial segmented profiles of various different radial segments are acquired and the total number of radial segmented profiles acquired per RR-interval is set to equal 1/R×the minimum number of radial segmented profiles necessary to give a fully sampled data set; in subsequent RR-intervals, the order of radial segments for which radial segmented profiles are acquired is switched; and wherein during image reconstruction a fully sampled data set for a given pre-determined heart phase is generated by sampling of raw data from radial segmented profiles acquired for said pre-determined heart phase and at least R−1 subsequent heart phases and/or by sampling of raw data from radial segmented profiles acquired for said pre-determined heart phase of at least R consecutive RR-intervals.

In order to allow for reconstruction of full data sets, the minimum number of shots encompassed by the pulse sequence can be set to equal at least the minimum number of radial segmented profiles necessary to give a fully sampled data set for each pre-determined heart phase.

The inversion pulse used in the method of the invention can be set to cause a deflection of 160° to 200°, preferably of 180°. The inversion pulse can be adiabatic.

SSFP (steady-state free precession) cine data acquisition in the method of the invention can be balanced or non-balanced.

In the method of the invention, the acquisition duration AD can be set to be not shorter than the time required to cover at least two full RR-intervals, preferably not shorter than the time required to cover at least three full RR-intervals. Alternatively, the acquisition duration AD may be set in relation to the maximum expected T1 of the tissue of interest, e.g. the acquisition duration AD may be set to 3-times the maximum expected T1 of the tissue of interest.

The relaxation duration RD in the method of the invention follows immediately adjacent to the acquisition duration AD, and RD can be set to last at least until the start of the next full RR-interval, preferably the relaxation duration RD is set to be not shorter than the time required to cover at least two full RR-intervals, even more preferably the relaxation duration RD is set to be not shorter than 5-times the maximum expected T1 time of the tissue of interest. After the RD, the next shot is started with a new inversion pulse as soon as the next ECG trigger is received.

Basically image reconstruction can be performed by using algorithms and methods known to the person skilled in the art.

In the method of the invention, reconstruction of T1 maps for a pre-determined heart phase can be performed by reconstructing a fully sampled data set from data of all radial segmented profiles acquired for said particular heart phase within the RR-intervals encompassed during the acquisition duration AD of one, more than one or all shots of the pulse sequence, followed by curve fitting and deviation correction. Suitable curve fitting algorithms are known in the art (see e.g. Sass et al., "Error analysis for optimized inversion recovery spin-lattice relaxation measurements", *J. Magn. Reson.* (1977), 25:263-276) and encompass non-linear three-parameter curve fitting using e.g. Levenberg-Marquardt algorithm. In particular, three-parameter curve fitting and deviation correction as described for standard Look-Locker pulse sequences can be used (see e.g. Deichmann et al., "Quantification of T1 values by SNAPSHOT-FLASH NMR imaging", *J. Magn. Reson.* (1992), 96: 608-612).

Cine images for a pre-defined number of pre-determined heart phases can be reconstructed by sampling data of all radial segmented profiles acquired for said number of pre-determined heart phases that are beyond a time point $T1_{90\%}$, which is calculated by determining for each pixel the time point where magnetization has recovered by 90%, and averaging the results of all pixels.

IR-prepared images for a pre-determined heart phase can be reconstructed by sampling data of all radial segmented profiles acquired for said pre-determined heart phase.

The present invention is also directed to a computer program, which, after it has been loaded into a memory appliance of a data processing device, enables said data processing device to conduct a method of the invention.

The invention also encompasses a computer readable storage medium, on which a computer program is stored, which, after it has been loaded into a memory appliance of a data processing device, enables said data processing device to conduct a method of the present invention.

There is a wide range of potential applications for the method of the invention and in particular of cardiac T1 mapping (i.e. pixel-wise measurement and visualization of longitudinal relaxation time), including the analysis of myocardial edema after acute myocardial injury as well as the quantification of contrast uptake/washout in areas of focal or diffuse myocardial fibrosis. The present method allows to generate this information in particular also for small animals or subjects with a heart rate higher than 200 bpm.

The method of the present invention provides ECG-gated T1 maps and uses the acquired data to generate cine data sets and IR-prepared images at the same time, which enables simultaneous assessment of quantitative signal changes, cardiac function, and late gadolinium enhancement (after application of contrast media). This approach not only saves acquisition time, but also facilitates registration of the different modalities since all arise from the same source data.

There are several mechanisms by which the performance of the technique can be adapted to given imaging needs:
a) acquisition duration AD and relaxation duration RD can be adjusted depending on the maximum expected T1 of the tissue of interest; e.g. 1500 ms for native myocardium, 1800 ms for blood, or 600 ms for post-contrast myocardium at 3 Tesla;
b) temporal undersampling or low numbers of cardiac phases can be used where the cine data with high resolution and/or quality is of less interest;
c) increasing the NSA (number of signal averages) is helpful where optimal signal-to-noise ratio is required.

In contrast to other T1 mapping approaches, where the relaxation curve is influenced at intervals determined by individual heart rate, there is no significant heart rate dependency for T1 values obtained with the method of the present invention since there is a permanent readout of predefined acquisition duration AD (e.g. 4000 ms) that does not change with heart rate. The only source of heart rate influence is given by the waiting time from the end of the predefined relaxation duration RD to the next ECG trigger, which is shorter than one RR interval (e.g. <200 ms at a heart rate of 300 bpm) and therefore negligible with typical choices of parameters (e.g. AD 4000 ms, RD 2000 ms).

The present invention is also directed to a method for use in conducting cardiac MR imaging which allows for reconstruction of T1 maps, cine images and IR-prepared images from one single raw data set, wherein the method comprises the following steps:
a) acquisition of raw data by use of an ECG-triggered, inversion recovery (IR)-prepared Look-Locker type pulse sequence for data acquisition, wherein the pulse sequence encompasses more than one shot, wherein each shot comprises:
  i) an ECG-triggered inversion pulse;
  ii) SSFP cine data acquisition of profiles over more than one RR-interval for a predefined acquisition duration AD; and
  iii) a relaxation duration RD, during which no data is acquired;
b) retrospective gating of raw data by sorting acquired raw data for each RR-interval into a pre-determined number of heart phases by definition of specific time windows within the RR-intervals and sampling of raw data acquired during the time windows respectively;
c) image reconstruction, wherein the retrospectively gated raw data is used for reconstruction of T1 maps, cine images and/or IR-prepared images.

This method differs from the method mentioned above by the fact that segmentation of profiles acquired during SSFP cine data acquisition is an optional feature, and by the fact that SSFP cine data acquisition can be performed radially or non-radially, e.g. cartesian.

In the method of the invention, the time between the ECG-trigger and release of the inversion pulse can be different between shots.

Example embodiments will now be described more fully hereinafter with reference to the accompanying figures.

BREIF DESCRIPTION OF THE DRAWINGS

Figures:
A brief description of the figures is given.

FIG. 1: illustrates the pulse sequence scheme of the method of the invention.

Figure 2:
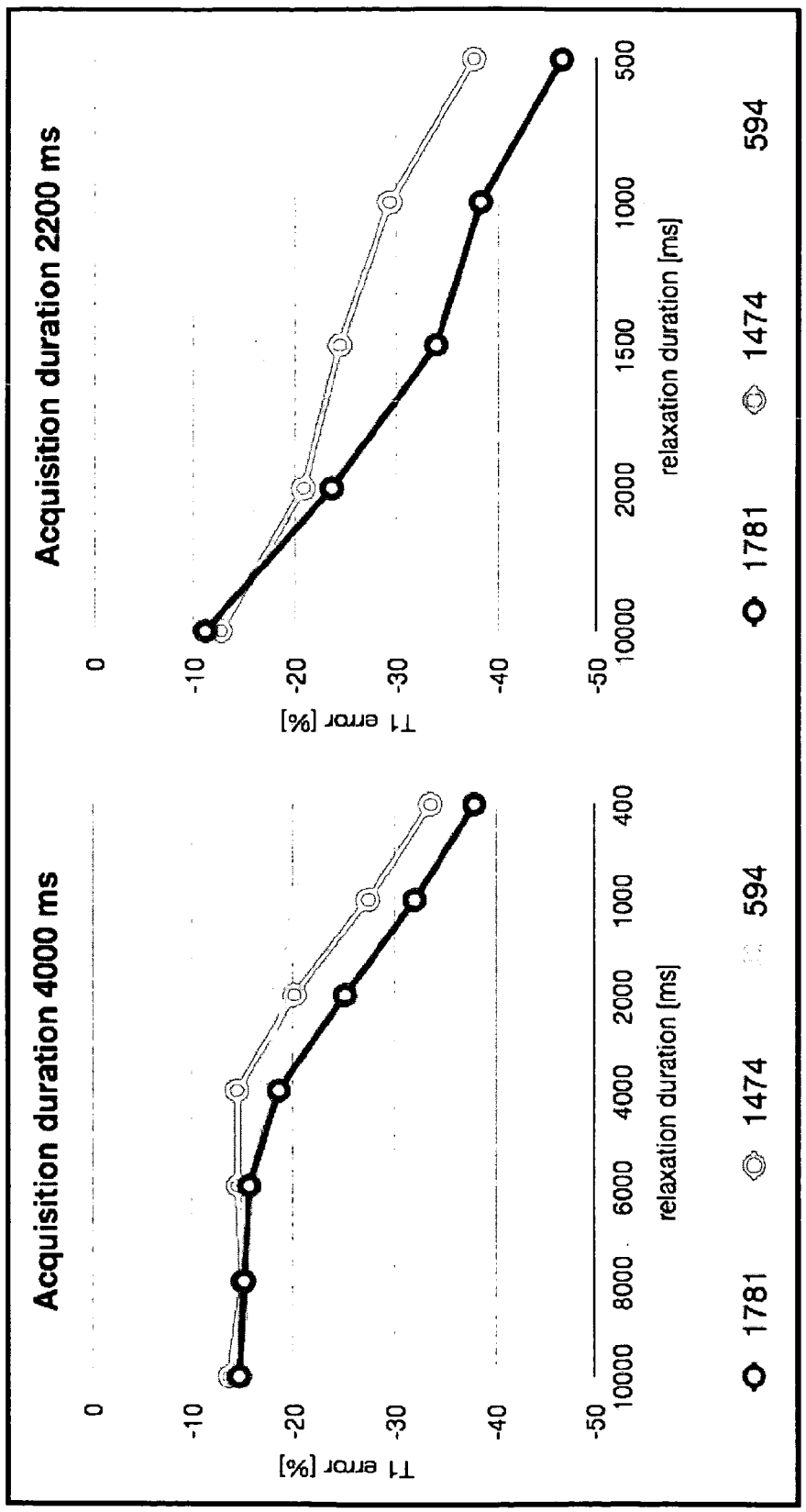

FIG. 2: shows percentage error of T1 measurements according to the method of the invention with two different acquisition durations and varying relaxation durations in phantoms with different T1 (594, 1474, and 1781 ms). An acquisition duration of 4000 ms in combination with relaxation duration of ≥5000 ms yields a stable underestimation of T1 by approximately 15% even for long T1 (1781 ms) as found in blood at 3 Tesla. An acquisition duration of 2200 ms together with relaxation duration of 1000 ms achieves systematic underestimation of <20% for T1 ≤600 ms (as found after injection of Gd-DTPA).

Figure 3:
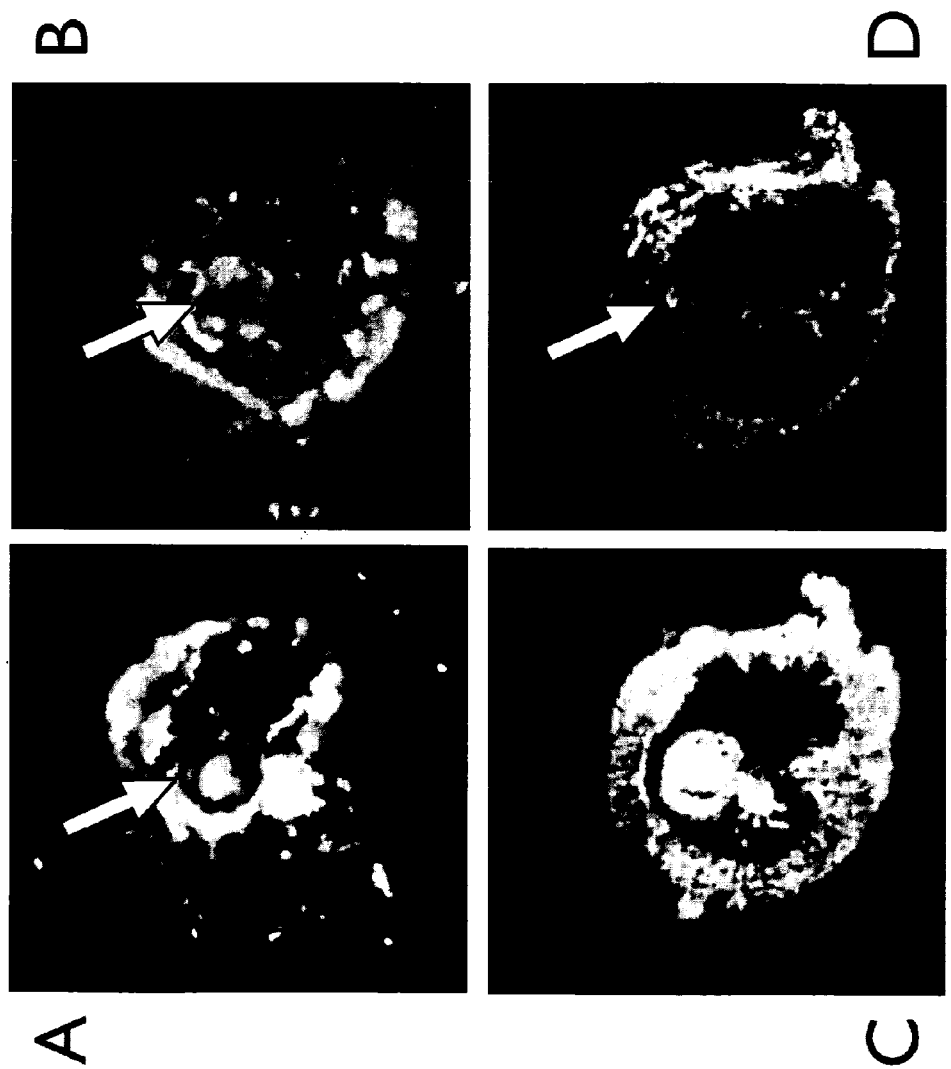

FIG. 3: shows pre-contrast T1 map (A), post-contrast T1 map (B), diastolic cine image (C), and IR-prepared "late gadolinium enhancement" image (D) of a rat with acute anterior myocardial infarction. The area of infarction (arrow) is characterized on these images by high T1 prior to contrast application (caused by myocardial edema), shortened T1 ten minutes after application of Gd-DTPA, regional hypokinesia, and hyper-enhancement, respectively.

Figure 4:
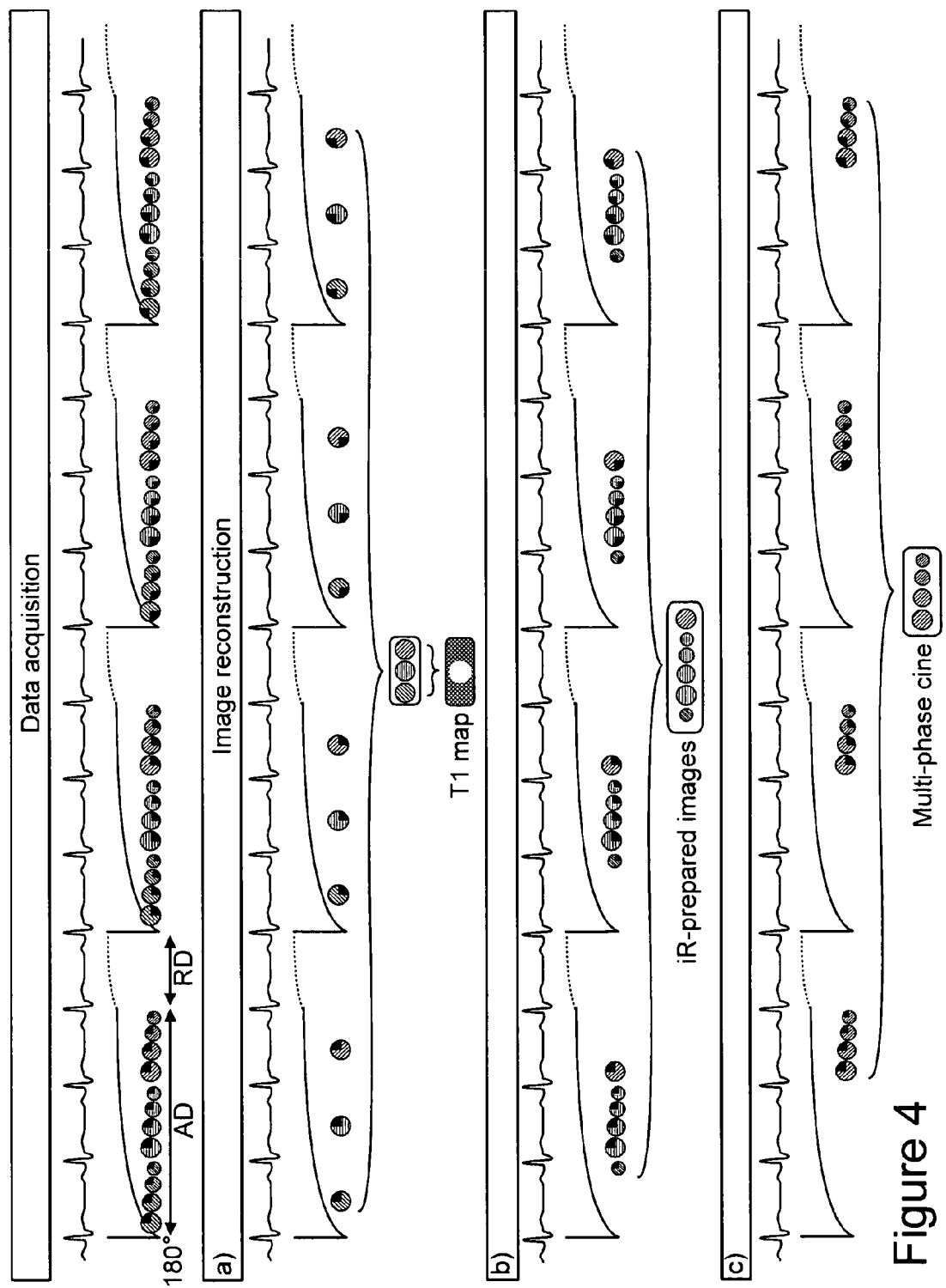

FIG. 4. Top: shows the pulse sequence scheme of the method of the invention; a) shows reconstruction of T1 maps; b) shows reconstruction of IR-prepared images; c) shows reconstruction of cine images.

Figure 5:
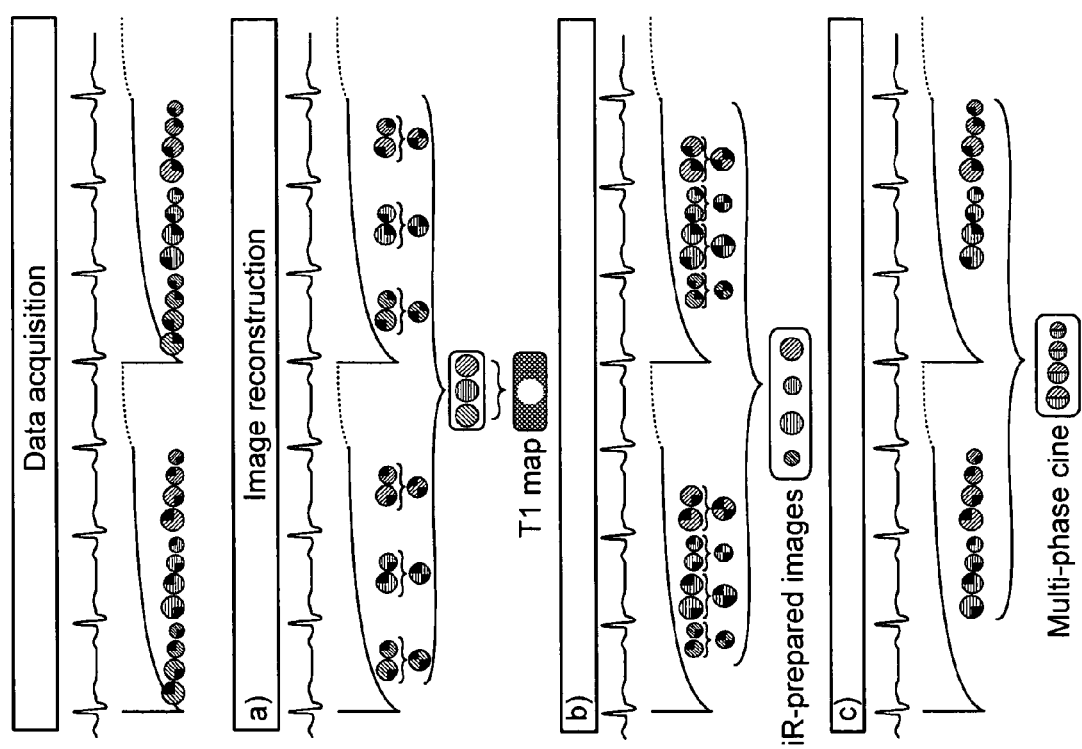

FIG. 5. Top: shows temporal undersampling for data acquired by the method of the invention; reconstruction of T1 maps (a), IR-prepared images (b) and cine images (c) is shown based on undersampled data.

Figure 6:
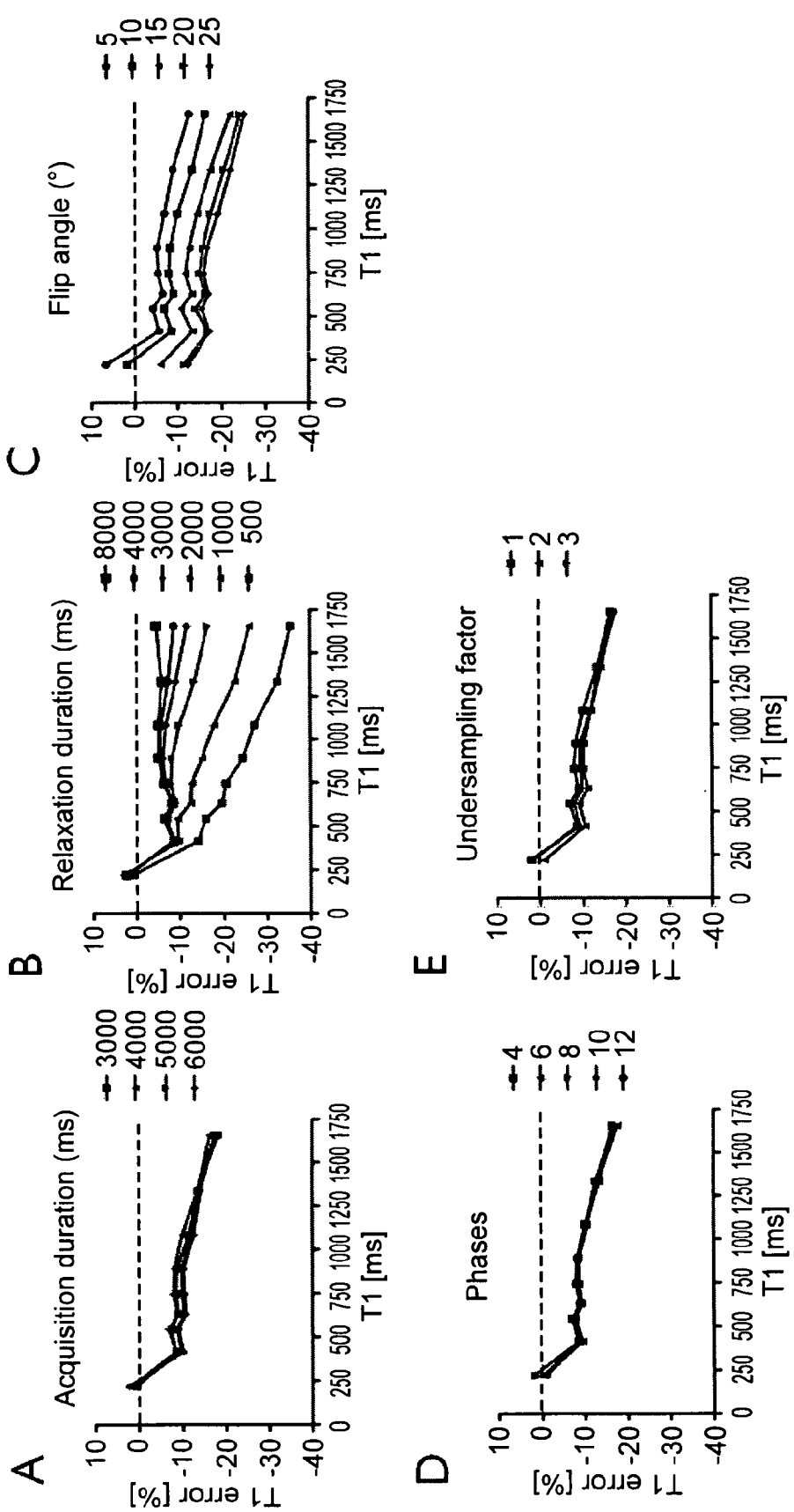

FIG. 6. shows accuracy of T1 maps prepared with the method of the invention depending on sequence parameters (A-E) expressed as percental T1 error from nominal T1 (as determined by a standard inversion recovery technique).

Figure 7:
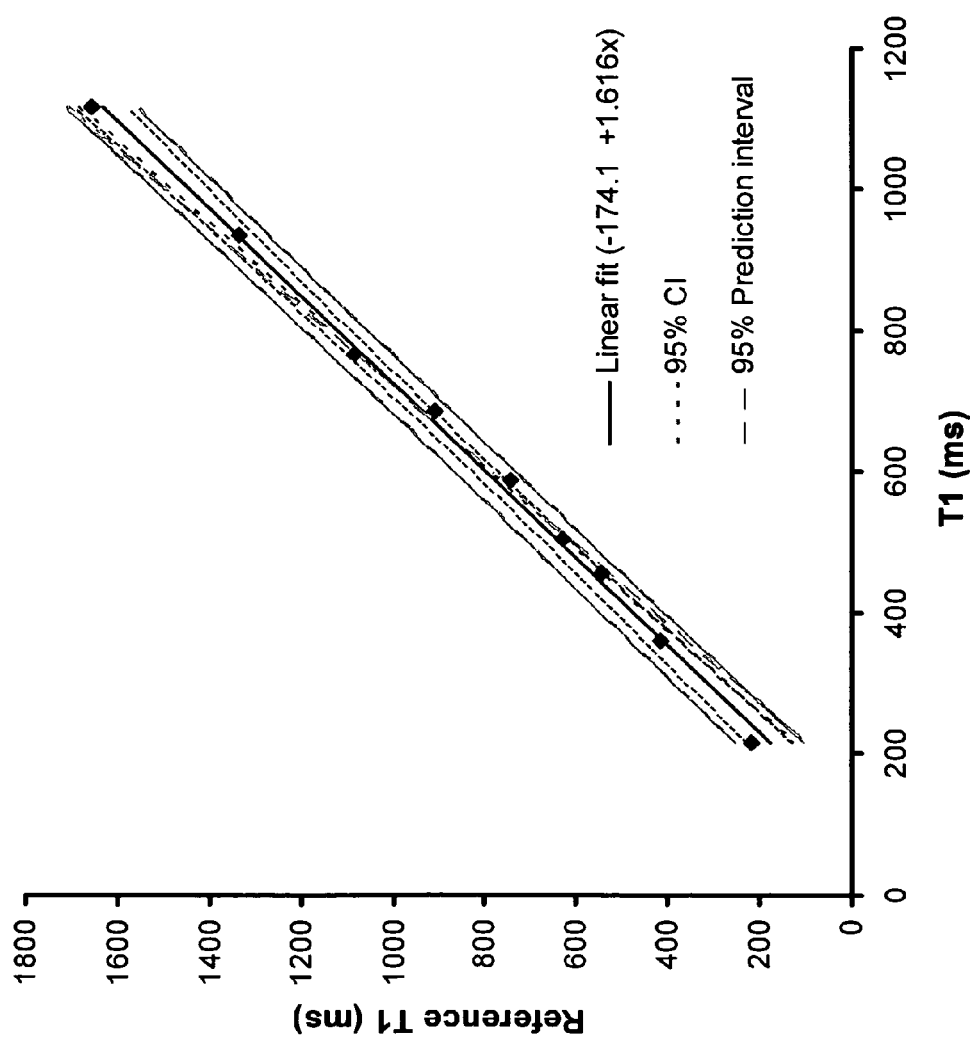

FIG. 7. shows regression analysis of the scheme of the method of the invention with high AD/RD ratio showing a strong linear relationship ($R^2$=1.00, p<0.0001) between T1 determined according to the invention and nominal T1 over the tested range. CI=confidence interval.

Figure 8:
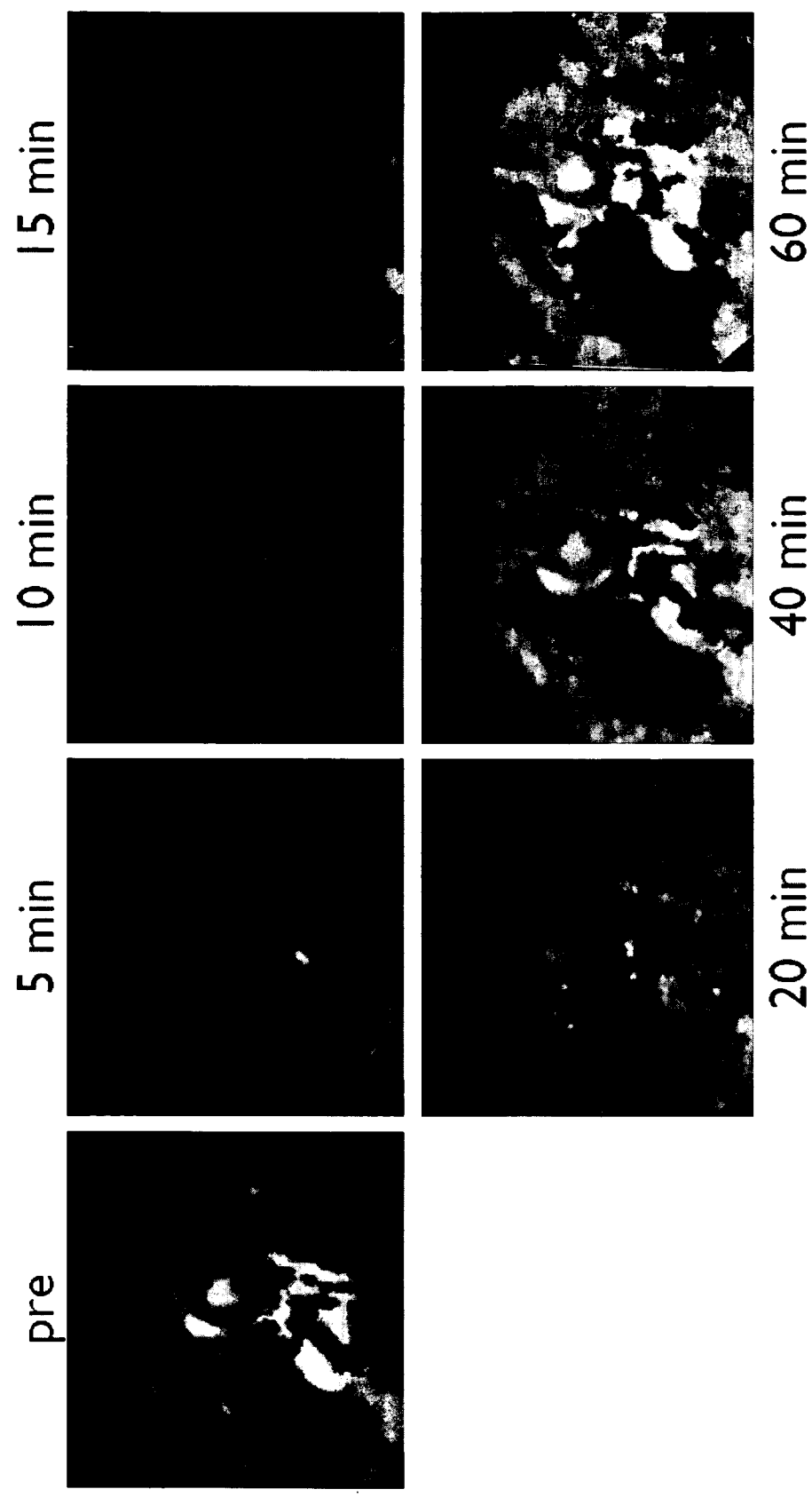

FIG. 8. shows a representative set of T1 maps before (pre) and after (5 to 60 minutes) intravenous application of Gd-DTPA in a healthy male Sprague-Dawley rat. Field-of-view 65×65 mm, pixel size 0.60×0.60 mm, slice thickness 3.0 mm, TR 5.2 ms, TE 2.2 ms, FA 10°, AD 5000 ms, RD 500 ms, phases 6.

Figure 9:
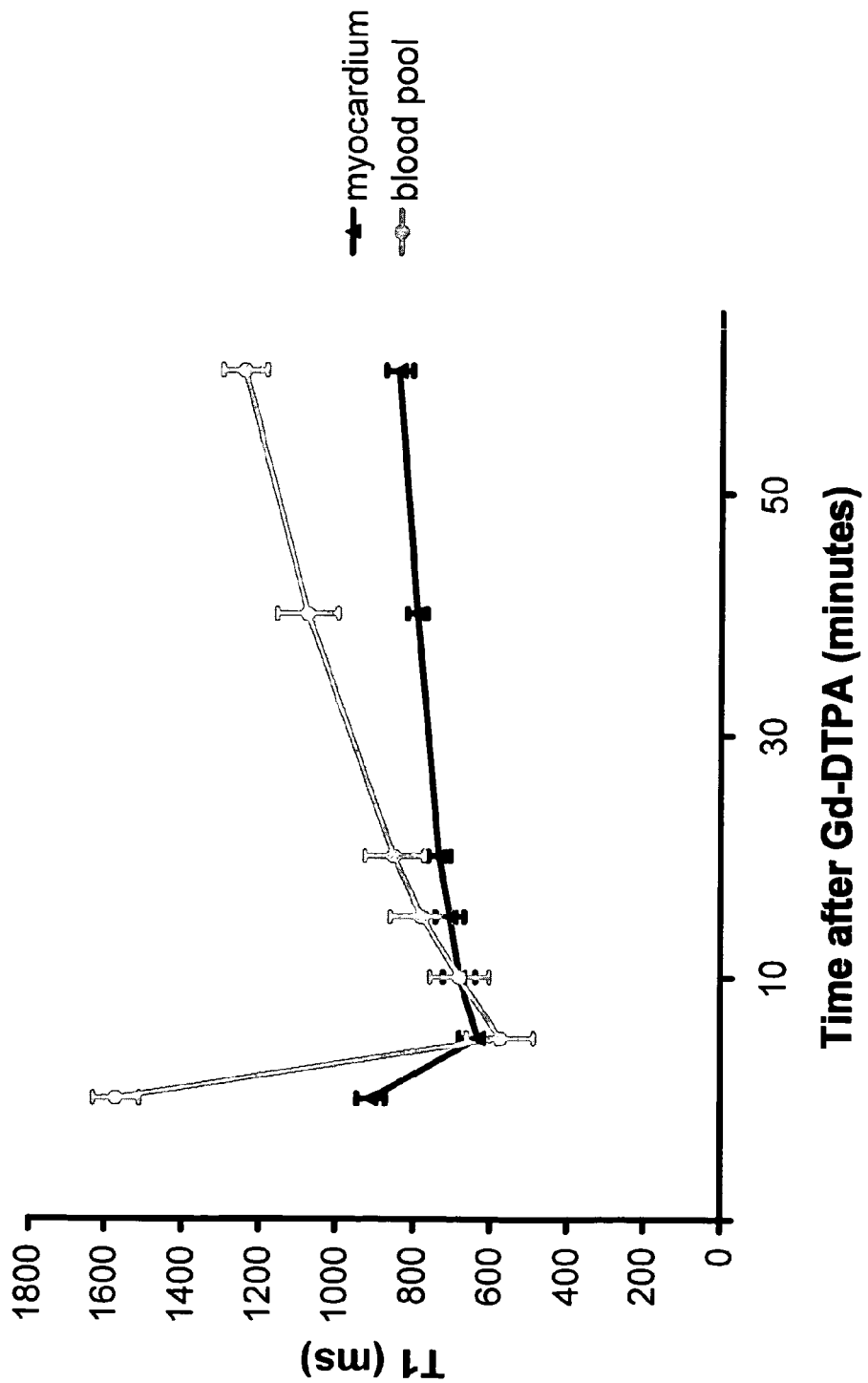

FIG. 9. shows T1 values (mean±standard deviation) of left ventricular myocardium and blood pool in 10 male Sprague-Dawley rats before(=0 minutes) and after intravenous administration of Gd-DTPA (0.1 mmol/kg).

Figure 10:
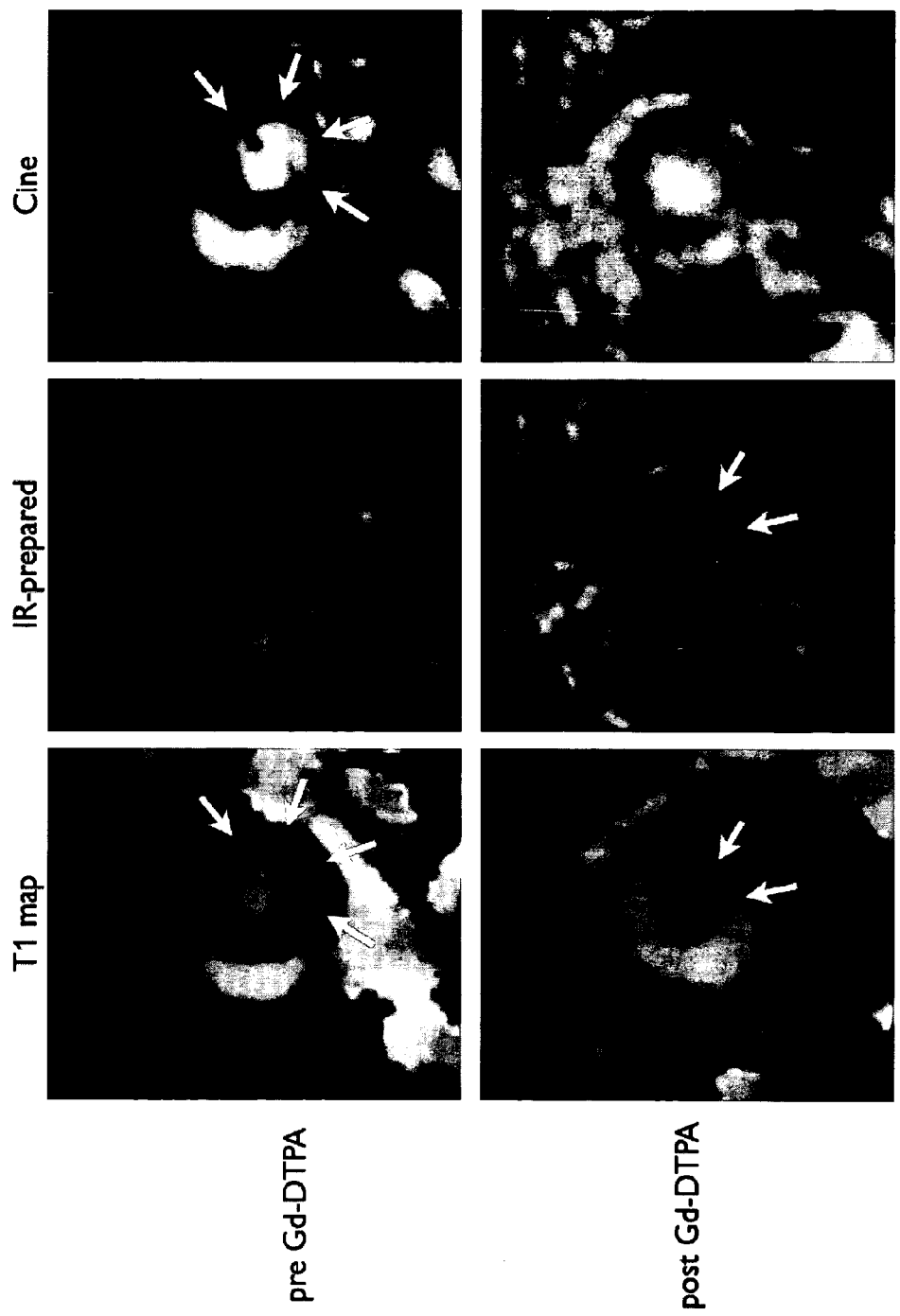

FIG. 10. shows In-vivo images prepared according to the invention from a rat with acute myocardial infarction (heart rate 290 bpm).

DETAILED DESCRIPTION OF THE PRESENTLY PREFERRED EMBODIMENTS

EXAMPLES

Example 1

Methods:
The method of the invention combines an adapted segmented, retrospectively gated, IR-prepared Look-Locker type pulse sequence with a multimodal reconstruction framework.

Pulse Sequence Details:
FIG. 1 illustrates the pulse sequence scheme. After an ECG-triggered non-selective (adiabatic) inversion pulse, n radial profiles of the first phase of the cardiac cycle are read out by a non-balanced steady-state free precession (SSFP) sequence, immediately followed by the read-out of the same n radial profiles of the second phase of the cardiac cycle and so on for a predefined period of time ("acquisition duration"). Upon completion of a predefined waiting period ("relaxation duration"), the next set of n radial profiles of the first phase of the cardiac cycle is read out, immediately followed by the same next set of n profiles of the second phase of the cardiac cycle and so on. The number of cardiac cycles (cc) covered by each acquisition step is given by cc=acquisition duration[s]× heart rate[/min]/60. The total scan time is determined by the number of lines prescribed for acquisition, the number of heart phases to be generated for cine images, the number of signal averages (NSA), and the minimal time of repetition (TR) of the read-out sequence. Two methods are implemented that can be used separately or in combination to accelerate the acquisition: radial undersampling and temporal undersampling. Radial undersampling allows reducing the density of angles used for composition of radial image data. Temporal undersampling allows reducing the number of frames within a cardiac cycle that are necessary to reconstruct a predefined number of cardiac phases.

Image Reconstruction:
Reconstruction of the acquired image data is performed off-line, either during the scanning session on the host computer of the MRI system or after the session on a separate computer, using a customized reconstruction framework (ReconFrame, Gyrotools, Zurich, Switzerland) implemented with MathLab (The MathWorks, Natick Mass., USA). Currently three types of images are reconstructed:

T1 maps: For each cardiac cycle encompassed by the acquisition, a raw image is reconstructed from all available image data acquired during a predefined time window within the RR interval. From these raw images, a T1 map is generated by performing 3-parameter Marquardt-Levenberg curve fitting for each pixel. Values are corrected for deviations caused by the Look-Locker type read out as described in the literature.

Cine images: Using the T1 map, the time point within the acquisition duration is determined where all longitudinal magnetization within the field of view has recovered by at least r % ($T1_{r\%}$). Cine images for a predefined number of cardiac phases are reconstructed from all image data available for each phase beyond $T1_{r\%}$. If temporal undersampling by a factor u is used for image acquisition, full image data sets are reconstructed by combining u neighbouring data sets.

IR-prepared images: For a predefined time interval after inversion, a set of IR-prepared images with predefined steps of inversion time (TI) is reconstructed from all image data available within the time interval.

MRI Experiments:

All experiments were carried out on a whole-body 3 Tesla MRI system (Achieva, Philips Medical System, Best, The Netherlands) equipped with a QuasarDual gradient system (80 mT/m, 200 mT/m/ms slew rate), using a dedicated solenoid coil for rat hearts.

Phantom studies: T1 accuracy of the method of the invention depending on relaxation duration was assessed in three fluid phantoms with nominal T1 values of 594, 1474, and 1781 ms for two different acquisition durations (4000 ms and 2200 ms). An internal ECG simulator was used to simulate a heart rate of 300/min.

In-vivo studies: The method was performed in two 12-week-old Sprague-Dawley rats, with one of them having undergone surgical ligation of the left anterior descending coronary artery (LAD) 12 h prior to MRI in order to create an acute anterior myocardial infarction. For MRI, animals were anesthetized with Isoflurane and placed onto an animal cradle. ECG signal was derived from electrodes attached to the skin. After collection of native data, contrast agent (gadolinium dimeglumine, 0.3 mmol/kg) was applied via a 26 G cannula placed into a tail vein, and further data were acquired.

Results:

FIG. 2 illustrates the results of the phantom measurements. With 4000 ms of acquisition duration, there is a systematic underestimation of T1 by approximately 15% as long as relaxation duration reaches 4000 ms (for maximal T1 times of 1500 ms) or 5000 ms (for maximal T1 times of 1800). With 2200 ms of acquisition duration, there is a systematic underestimation of T1 by approximately 18% for a T1 value of 600 ms as long as relaxation duration reaches 1000 ms. Other imaging parameters included: cardiac phases 12, field-of-view 64×64 mm, voxel size 0.6×0.6×3.0 mm, NSA 2, temporal undersampling factor 2, density of angles 100%, flip angle 10°, TR 5.4 ms, TE 2.3 ms.

FIG. 3 shows images acquired in-vivo using a 4000/5000 (acquisition/relaxation duration) scheme for pre-contrast and a 2200/1000 scheme for post-contrast situations.

Example 2

Materials and Methods

Animal studies were approved by the local animal care committee and performed according to Good Laboratory Practice guidelines.

All experiments were carried out on a whole-body 3 Tesla MR system (Achieva, Philips Medical Systems, Best, The Netherlands) equipped with a QuasarDual gradient system (80 mT/m, 200 mT/m/ms slew rate) and a 70 mm solenoid coil for rat hearts.

Pulse Sequence Scheme

FIG. 4 shows the pulse sequence scheme for fully sampled data sets (top) and reconstruction of multi-modal images (a-c). FIG. 5 illustrates the principles of "temporal undersampling", which was implemented to accelerate the acquisition.

Reconstruction of the acquired image data was performed using a customized reconstruction framework (ReconFrame, Gyrotools, Zurich, Switzerland) implemented with Matlab (The MathWorks, Natick Mass., USA). For T1 maps, 3-parameter curve fitting was performed for each pixel as used for standard Look-Locker pulse sequences using $$M = A - B \exp(-t/T1^*) \quad [1]$$

and calculating T1 from $$T1 = T1^*[(B/A) - 1] \quad [2]$$

(M=signal intensity; A=scaling factor for equilibrium magnetization $M_0$; B=correction factor for imperfect inversion; t=effective inversion time).

A set of IR-prepared images with predefined steps of inversion time (TI) was reconstructed from all image data available within the time interval.

Using the T1 map, the time point within the acquisition duration was determined where all longitudinal magnetization within the field of view had recovered by at least 90% ($T1_{90}$). Cine images for a predefined number of cardiac phases were reconstructed from all image data available beyond $T1_{90}$.

FIG. 4. Top: pulse sequence scheme of the method of the invention is shown. After an adiabatic inversion pulse (180°), image data for the first radial segment (segments=colored sectors of circles) are continuously sampled for consecutive phases (circles of different sizes) and heart cycles (different circle colors) during a predefined acquisition duration (AD), while magnetization recovers with a time constant T1* (solid line). After a predefined relaxation duration (RD), during which magnetization recovers without any readout-induced perturbations with a time constant T1 (dashed line), the process is repeated for the next radial segment and so on.

a) Reconstruction of T1 maps. In a first step, raw images for the number of cardiac cycles encompassed by AD are reconstructed from all available image data acquired during a predefined time window within the RR interval, e.g. during systole. In a second step, pixel-wise non-linear curve fitting is performed and the resulting T1* values are corrected for readout-induced deviation of the magnetization recovery curve in order to generate a T1 map from these raw images.

b) Reconstruction of IR-prepared images. For a predefined time interval after inversion, a set of IR-prepared images with predefined steps of inversion time (TI) is reconstructed from all image data available within the time interval.

c) Reconstruction of cine images. Cine images for a predefined number of cardiac phases are reconstructed from all image data available beyond $T1_{90\%}$.

FIG. 5. Top: Undersampled data acquisition according to the method of the invention (undersampling factor R=2). Data of each radial segment is only acquired at every other phase of one heart cycle. At the next heart cycle, the order of acquisition of the segments is switched. For reconstruction of T1 maps (a), raw images are generated by combining data from neighboring phases, which then are further processed. The same approach is used for IR-prepared images (b). For cine images, data from neighboring heart cycles are combined to generate full data sets maintaining the same temporal resolution as for full data sampling (c).

Phantom Studies

The influence of different pulse sequence parameters (acquisition duration=AD, relaxation duration=RD, flip angle, phases, temporal undersampling factor) on T1 accuracy of the method of the invention was tested in 9 agarose gel phantoms doped with different amounts of gadolinium. Nominal T1 of the phantoms was determined using a standard multi-IR gradient echo technique. For measurements, an internal ECG simulator was used to simulate a heart rate of 300 bpm. T1 times were derived from the resulting T1 maps for regions-of-interest in each phantom using OsiriX v3.7.

Common pulse sequence parameters included field-of-view 65×65 mm, pixel size 0.60×0.60 mm, slice thickness 3.0 mm, TR 5.2 ms, TE 2.2 ms.

As for other IR-based imaging techniques, it could be expected that the choice of $RD<5*T1_{max}$ would lead to underestimation of long T1 times due to incomplete recovery of longitudinal magnetization. To test if this T1 underestimation could be corrected for, additional phantom T1 maps were acquired using a scheme in accordance with the method of the invention with high AD/RD ratio (AD 5000 ms, RD 500 ms). Linear regression analysis was performed to analyze the relationship between T1 as determined by the method of the invention and reference T1 values (Analyse-it 2.11, Analyse-it Software, Leeds, UK).

In-Vivo Studies 10 male Sprague-Dawley rats (body weight 441±27.5 g, mean±standard deviation) were examined in short-axis orientation before and at 5, 10, 15, 20, 40, and 60 minutes) after intravenous application of gadopentetate dimeglumine (Gd-DTPA; Magnevist®, Bayer Schering Pharma AG, Berlin, Germany; 0.1 mmol/kg). During the MR examination, anesthesia was maintained with inhalative isoflurane (1.5%), and ECG was derived from electrodes attached to the shaved chest and lower abdomen of the animal. Geometrical parameters were the same as for the phantom measurements. T1 maps were reconstructed at end-systole. Mean T1 of left-ventricular myocardium and blood pool were derived from regions-of-interested (cmr42, Circle Cardiovascular Imaging, Calgary, AB, Canada). Surgical ligation of the left circumflex artery was carried out in one additional male Sprague Dawley rat, and MRI according to the method of the invention was performed before and after the intravenous application of Gd-DTPA (0.3 mmol/kg), starting 8 hours after surgery.

Results

Nominal T1 of the phantoms ranged from 240 to 1656 ms. FIG. 6 shows the results of the phantom experiments. FIG. 6. Accuracy of T1 determined in accordance with the method of the invention maps depending on sequence parameters (A-E) expressed as percental T1 error from nominal T1 (as determined by a standard inversion recovery technique). The choice of RD (B) and flip angle (C) have the strongest impact on T1 accuracy. Other pulse sequence parameters: simulated heart rate 300 bpm, field-of-view 65×65 mm, pixel size 0.60× 0.60 mm, slice thickness 3.0 mm, TR 5.2 ms, TE 2.2 ms.

The number of phases had almost no impact on T1 accuracy. The strongest aberrations were observed for large flip angles and short RDs. Regression analysis of the pulse scheme of the invention with high AD/RD ratio showed a strong linear relationship ($R^2=1.00$, p<0.0001) between T1 determined in accordance with the method of the invention and nominal T1 over the entire range tested, see FIG. 7, regression analysis of the scheme of the method of the invention with high AD/RD ratio showing a strong linear relationship ($R^2=1.00$, p<0.0001) between T1 determined by the method of the invention and nominal T1 over the tested range. CI=confidence interval. Using the resulting slope and intercept for T1 correction ($T1_{corrected}=T1_{invention}\times1.616-174.1$), relative error of T1 could be reduced to 1.3±7.4%.

In the group of healthy rats, 67 out of 70 (10 animals, 7 time points each) T1 maps could be successfully acquired with the method of the invention; 3 T1 maps could not be acquired due to poor ECG triggering. FIG. 8 shows a representative set of T1 maps before and after application of Gd-DTPA. FIG. 9 illustrates the results of corrected myocardial and blood T1 values.

FIG. 10 shows in-vivo images of the rat with acute myocardial infarction based on data acquired using the method of the invention. FIG. 10, shows in-vivo images from a rat with acute myocardial infarction (heart rate 290 bpm). Before administration of Gd-DTPA (top row), the infarction can be identified as an area of elevated T1 (white arrows) on the T1 map (left), representing myocardial edema. The systolic cine image (right) demonstrates severe hypokinesia and reduced wall thickening in the same area. Twenty minutes after the administration of Gd-DTPA (bottom row), the area of necrosis, which is smaller than the area of myocardial edema, is delineated by both the T1 map (shortened T1) and the IR-prepared image (hyperenhancement) due to late gadolinium enhancement. Field-of-view 65×65 mm, pixel size 0.60×0.60 mm, slice thickness 3.0 mm, TR 5.2 ms, TE 2.2 ms, FA 10°, AD 4000 ms, RD 2000 ms, phases 12 (before Gd-DTPA)/6 (after Gd-DTPA). On the pre-contrast T1 map, the infero-lateral wall exhibited prolonged T1 values (indicating myocardial edema) as compared to remote areas (1031±18 vs 942±33 ms). Pre-contrast cine images with a temporal resolution or 12 phases per cardiac cycle revealed a marked wall motion abnormality in the same area. On the post-contrast T1 map, the center of the infero-lateral wall showed severely reduced T1 times (438±49 ms) as compared to remote areas (632±47 ms), indicating myocardial necrosis. On visual assessment, the extent of this area corresponded to that of hyper-enhancement on the IR-prepared image (conventional late gadolinium enhancement), but was smaller than that of T1 prolongation on the pre-contrast T1 map.

Discussion

Our study presents a cardiac MR method that uses a specifically ordered acquisition strategy and a multi-modal image reconstruction approach. The method enables simultaneous generation of cardiac T1 maps, cine, and IR-prepared images at high heart rates, allowing for time-efficient assessment of T1 properties, function, and late gadolinium enhancement from one single set of image data.

The results of the phantom measurements show that there is systematic underestimation of T1, which could be expected for a segmented Look-Locker approach. In general, (non-balanced) read-out pulses lead to a deflection of the relaxation curve, causing magnetization to yield a steady state with a time constant T1* instead of T1 Higher read-out pulses aggravate this phenomenon. Additionally, short RD prevents full recovery of magnetization for voxels of high T1 introducing T1-dependent inaccuracies of the measurements. Our results show that these effects can be strongly reduced by the use of a simple linear correction algorithm.

The in-vivo experiments demonstrate the potential of the present method for a comprehensive assessment of myocardial injury. In the group of normal rats, T1 of myocardium and blood pool exhibited narrow ranges of normal both prior to and after the application of Gd-DTPA. T1 values were in good agreement with previous results of rat studies from the literature. Such homogenous behavior of normal tissue represents an important prerequisite for future applications, e.g. for in-vivo quantification of diffuse myocardial fibrosis in animal models of left ventricular hypertrophy. In the rat with acute myocardial infarction, before the administration of contrast agent, T1 map and cine images served to identify the "area at risk" as a zone of elevated T1 caused by myocardial edema.

After the application of Gd-DTPA, T1 map and IR-prepared (late gadolinium enhancement) image enabled delineation of the necrosis. From these limited data it appears that the present method allows both morphologic and functional characterization of different tissue states in both qualitative and quantitative ways.

The method presented generates three types of images from one image data set. Apart from the time saving effect, this approach also carries the advantage that images of corresponding heart phases from all three modalities always spatially match each other. Thus, direct comparison of findings is possible without the need for further registration of the images. However, it might still be reasonable to adjust imaging parameters in order to optimize the acquisition for the given diagnostic needs. For example, for the in-vivo images of the animal with acute myocardial infarction we decided to reduce scan time of the post-contrast data at the cost of temporal resolution of the cine images since the functional information was already available from the pre-contrast data. Accordingly, the choice of imaging parameters might be different in experimental settings where global myocardial changes are to be expected as opposed to those where focal changes are of interest.

An implementation on ultra-high-field systems, as frequently used for small animal MRI, is feasible without major modifications and will benefit from shorter repetition times due to faster gradient systems available on dedicated small animal MR scanners. Another interesting extension of the technique is the use of balanced SSFP read-out pulses, which will provide higher signal-to-noise ratio. This will require efficient strategies for shimming of small volumes and for reduction of off-resonance artifacts (e.g. wide-band SSFP), which are common challenges with balanced SSFP at field strengths of 3 Tesla or above.

The characterization of myocardial properties using cardiac T1 mapping is attracting more and more interest because of its quantitative approach and the resulting potential to detect diffuse processes. The method of the invention allows for systematic studies of T1 behavior in small-animal models of myocardial injury, which should help to better define the role of cardiac T1 mapping in clinical MRI. The simultaneous assessment of cardiac function and myocardial properties enables studies on the chronological formation of myocardial injury. The concept of multi-modal data acquisition and image generation is also of interest for human applications, where a pulse sequence providing late gadolinium enhancement images and T1 maps at the same time could present the missing link between qualitative and quantitative assessment of the myocardium.

The invention claimed is:

1. A method for use in conducting cardiac magnetic resonance (MR) imaging, which allows for reconstruction of T1 maps, cine images and inversion recovery (IR) prepared images from one single raw data set, wherein the method comprises the following steps:
    a) acquisition of raw data from a cardiac tissue by use of an electrocardiogram (ECG) triggered, segmented, inversion recovery (IR)-prepared Look-Locker type pulse sequence for data acquisition, wherein the pulse sequence encompasses more than one shot, wherein each shot comprises:
        i) an ECG-triggered inversion pulse;
        ii) continuous steady-state free precession (SSFP) cine data acquisition of radial segmented profiles over more than one cardiac cycle (RR-interval) for a pre-defined acquisition duration AD; and
        iii) a relaxation duration RD, during which no data is acquired;
    b) retrospective gating of the raw data by sorting the acquired raw data for each RR-interval into a pre-determined number of heart phases by definition of specific time windows within the RR-intervals and sampling of raw data acquired during the time windows respectively;
    c) reconstructing images, wherein the retrospectively gated raw data is used for reconstruction and wherein the reconstructed images are T1 maps, cine images and/or IR-prepared images.

2. The method of claim 1, wherein SSFP cine data acquisition of radial segmented profiles is performed such that all radial segmented profiles acquired during one shot cover a radial segment and the radial segment to be acquired and the order of radial segments for which readial segmented profiles are acquired is switched between subsequent shots.

3. The method of claim 1, wherein SSFP cine data acquisition of radial segmented profiles is performed such that a temporal undersampling factor R for the data acquisition is set; during raw data acquisition in each RR-interval radial segmented profiles of various different radial segments are acquired and the total number of radial segmented profiles acquired per RR-interval is set to equal 1/R×the minimum number of radial segmented profiles necessary to give a fully sampled data set; in subsequent RR-interval the order of radial segments for which radial segmented profiles are acquired is switched; and wherein during image reconstruction a fully sampled data set for a given pre-determined heart phase is generated by sampling of raw data from radial segmented profiles acquired for said pre-determined heart phase and at least R-1 subsequent heart phases and/or by sampling of raw data from radial segmented profiles acquired for said pre-determined heart phase of at least R consecutive RR-intervals.

4. The method of claim 1, wherein the minimum number of shots encompassed by the pulse sequence equals the minimum number of radial segmented profiles necessary to give a data set for each pre-determined heart phase.

5. The method of claim 1, wherein the inversion pulse is adiabatic.

6. The method of claim 1, wherein the inversion pulse is set to cause a deflection of 160° to 200°.

7. The method of claim 1, wherein SSFP used for cine data acquisition is balanced or non-balanced.

8. The method of claim 1, wherein the acquisition duration AD is set to be not shorter than 3-times the maximum expected T1 of the cardiac tissue.

9. The method of claim 1, wherein the acquisition duration AD is set to be not shorter than the time required to cover at least two full RR-intervals.

10. The method of claim 1, wherein the relaxation duration RD is set to last at least until a start of the next full RR-interval.

11. The method of claim 1, wherein reconstruction of T1 maps for a pre-determined heart phase is performed by reconstructing a data set from data of all radial segmented profiles acquired for said particular heart phase within the RR-intervals encompassed during the acquisition duration AD of one, more than one or all shots, followed by curve fitting and deviation correction.

12. The method of claim 1, wherein cine images for a pre-defined number of pre-determined heart phase are reconstructed by sampling data of all radial segmented profiles acquired for said number of a pre-determined heart phases that are beyond $T1_{90\%}$.

13. The method of claim 1, wherein IR-prepared images for a pre-determined heart phase are reconstructed by sampling data of all radial segmented profiles acquired for said pre-determined heart phase.

14. A non-transitory computer program, which, after the computer program has been loaded into a memory appliance of a data processing device, enables said data processing device to conduct a method according to claims 1.

15. A non-transitory computer readable storage medium, on which a computer program is stored, which, after the computer program has been loaded into a memory appliance of a data processing device, enables said data processing device to conduct a method according to claims 1.

16. The method for use in conducting cardiac magnetic resonance (MR) imaging which allows for reconstruction of T1 maps, cine images and inversion recovery (IR) prepared images from one single raw data set, wherein the method comprises the following steps:
   a) acquisition of raw data from a cardiac tissue by use of an electrocardiogram (ECG) triggered, inversion recovery (IR)-prepared Look-Locker type pulse sequence for data acquisition, wherein the pulse sequence encompasses more than one shot, wherein each shot comprises:
      i) an ECG-triggered inversion pulse;
      ii) continuous steady-state free precession (SSFP) cine data acquisition of profiles over more than one cardiac interval (RR-interval) for a predefined acquisition duration AD; and
      iii) a relaxation duration RD, during which no data is acquired;
   b) retrospective gating of the raw data by sorting the acquired raw data for each RR-interval into a pre-determined number of heart phases by definition of specific time windows within the RR-intervals and sampling of raw data acquired during the time windows respectively;
   c) reconstructing images, wherein the retrospectively gated raw data is used for reconstruction and wherein the reconstructed images are T1 maps, cine images and/or IR-prepared images.

17. The method of claim 16, wherein the profiles acquired during SSFP cine data acquisition are segmented.

18. The method of claim 17, wherein the profiles are segmented radially or cartesian.

19. The method of one of claims 16, wherein the time between the ECG-trigger and release of the inversion pulse can be different between shots.

20. A non-transitory computer program, which, after the computer program has been loaded into a memory appliance of a data processing device, enables said data processing device to conduct a method according to claims 16.

21. A non-transitory computer readable storage medium, on which a computer program is stored, which, after the computer program has been loaded into a memory appliance of a data processing device, enables said data processing device to conduct a method according to claims 16.

* * * * *